United States Patent [19]
Schabert et al.

[11] Patent Number: 6,068,988
[45] Date of Patent: May 30, 2000

[54] DETECTION OF MICROBIAL METABOLITES WITH A 3-INDOXYL-MYO-INOSITOL-1-PHOSPHATE COMPOUND

[75] Inventors: Günter Schabert, Goldach; Urs P. Spitz, St. Gallen; Roland Humm, Rorschach, all of Switzerland

[73] Assignee: Biosynth AG, Staad, Switzerland

[21] Appl. No.: 08/988,540

[22] Filed: Dec. 10, 1997

Related U.S. Application Data

[60] Provisional application No. 60/039,479, Feb. 28, 1997.

[51] Int. Cl.$^7$ .............................. C12Q 1/42; C12N 9/18; C07H 5/04; C07D 209/04
[52] U.S. Cl. ......................... 435/21; 435/197; 536/18.7; 548/469
[58] Field of Search .............................. 435/4, 7.72, 18, 435/19, 21, 195, 196, 198; 536/1.11, 18.7, 31; 534/790; 548/469, 508

[56] References Cited

U.S. PATENT DOCUMENTS 5,364,767  11/1994  Flowers et al. ........................ 435/39

OTHER PUBLICATIONS

Yarborough et al. "Histochemistry of Macrophage Hydrolases III. Studies on beta–Galactosidase, beta–Glucoronidase and Aminopeptidase wiyh Indolyl and naphthyl Substrates," J. Reticuloendothelial Soc. (1967) 4: 390–408.

Haugland, R.P. "Handbook of Fluorescent Probes and Research Chemicals," 5th edition. (1992) p. 81–88.

Horwitz et al. "Substrates for cytochemiccal demonstration of enzyme activity. V. Thymidine 3'–and 5'–(5–bromo–4–chloro–3–indolyl)phosphates," J. Med. Chem. (1970) 13(5): 1024–5. *This paper was included with but not listed on the IDS.

Hafner, et al., "Cyclohexyl Alkylphosphonofluoridates," J. Med. Chem., vol. 13, No. 5, 1025–1027 (1970).

Shashidhar, et al., "A Fluorescent Substrate for the Continuous Assay of Phosphatidylinositol–Specific Phospholipase C: Synthesis and Application of 2–Naphthyl myo–Insitol–1–phosphate," Anal. Biochem., 198:10–14 (1991).

Hendrickson, et al., "A Thiophosphate Substrate for a Continuous Spectrophotometric Assay of Phosphatidylinositol–Specific Phospholipase C: Hexadecylthiophosphoryl–1–myo–Inositol," Bioorganic & Medical Chemistry Letters, vol. 1, No. 11, pp. 615–618 (1991).

Shashidhar, et al., "A Chromogenic Substrate for Phosphatidylinositol–specific Phospholipase C: 4–nitrophenyl myo–inositol–1–phosphate," Chemistry and Physics of Lipids, 60:101–110 (1991).

Leigh, et al., "Substrate Stereospecificity of Phosphatidylinositol–Specific Phospholipase C from *Bacillus cereus* Examined Using the Resolved Enantiomers of Synthetic myo–Inositol 1–(4–Nitrophenyl phosphate)", Biochemistry (1992). vol. 31 No. 37 pp. 8978–8983.

Ryan, et al., "A Chemiluminescent Substrate for the Detection of Phosphatidylinositol–Specific Phospholipase C," Analytical Biochemistry, 214:548–556 (1993).

Primary Examiner—Jon P. Weber
Assistant Examiner—Susan Hanley
Attorney, Agent, or Firm—Blank Rome Comisky & McCauley LLP

[57] ABSTRACT

A method of detecting a phosphatidylinositol-specific phospholipase C enzyme by means of a substrate which is cleaved by said enzyme and yields a dye when the chromophoric portion of the substrate is dimerized and oxidized; the invention teaches using in such method, as a novel substrate, a 3-indoxyl-myo-inositol-1-phosphate compound of formula (I)

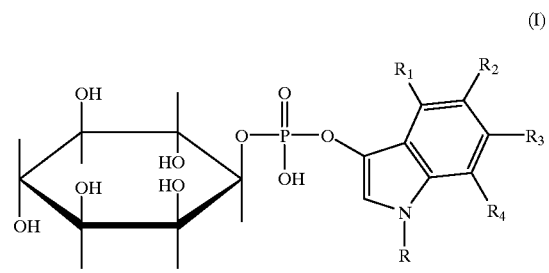

(I)

wherein R is selected from the group consisting of hydrogen and $C_{1-4}$ alkyl, while $R_1$, $R_2$, $R_3$, and $R_4$ are radicals selected from the group consisting of hydrogen, halogen, cyano, nitro, carboxy, amino, alkyl-substituted amino and sulphonyl; or of a salt of said formula I compound. The invention provides for a safe and sensitive method of detection of potentially pathogenic bacterial activity of such microbes as *Bacillus cereus, B. Thuringiensis*, Staphy lococcus aureus and various Listeria strains in potentially infected materials including physiological samples or consumable goods such as foods and beverages.

7 Claims, 3 Drawing Sheets

DETECTION OF MICROBIAL METABOLITES WITH A 3-INDOXYL-MYO-INOSITOL-1-PHOSPHATE COMPOUND

This application is a continuation-in-part of Provisional application Ser. No. 60/039,479, filed on Feb. 28, 1997, the subject matter of which is incorporated herein in its entirety.

FIELD OF THE INVENTION

The invention generally relates to the art of detecting microbial metabolites, i.e. substances secreted or otherwise produced by pathogenic microbes, and specifically to the detection of phosphatidyl-inositol-specific phospholipase C; the term "detection" is intended herein to include detection methods and assay techniques, substances or substrates for use in such methods, as well as novel compositions and substances.

PRIOR ART

It is known that certain enzymes, namely phosphatidylinositol-specific phospholipases C (also termed PI-PLCs herein) are found in the culture supernatants of several bacteria, and that detection of such enzymes is a valuable analytical tool for prophylactic as well as diagnostic use; in fact, several types of infection can be prevented if bacterial contamination, e.g. as evidenced by the presence of PI-PLCs, is found in products for consumption by, or contact with, humans, and actual infection can be diagnosed if such enzymes are found in physiological material obtained from a patient.

Of specific interest herein is the PI-PLC activity which is found in culture media of certain microbes, notably pathogenic strains of Listeria, Staphylococcus and Clostridium. Such interest is due both to the severity of pathological effects of these bacteria as well as to the problems of their reliable and easy detection.

Bacterial PI-PLCs are soluble enzymes which hydrolyse phosphatidylinositol (PI) and glycan-phosphatidinyl-inositol (GPI) but not PI-phosphates, whereas eukaryotic PI-PLCs are membrane-associated and $Ca^{2+}$-dependent enzymes which do hydrolyse both PI as well as PI phosphates.

In recent years, extensive biochemical studies were made with PI and its phosphorylated derivatives in eukaryotic cells in in order to research the pathways of signal transduction depending on inositol phosphates. These studies were hampered by the fact that suitable substrates for PI-PLC have not been available. Natural substrates, i.e. the phosphoinositides, cannot be used for this purpose because of the appearance of enzymatic products, i.e. diacylglycerol and myo-inositol phosphate(s) appear, or the disappearance of the substrate cannot be followed conveniently.

As a consequence most methods of determining PI-PLC activity made use of radiolabeled PI or radiolabeled surface glycoproteins which precludes continuous detection methods.

More recently, new synthetic substrates were developed. The first continuous assay of PI-PLC used 2-naphthyl myo-inositol-1-phosphate (2-NIP) as a substrate for fluorometric measurement of PI-PLC activity (cf. M. S. Shashidhar, J. J. Volwerk, J. F. W. Keana, O. H. Griffith; Anal. Biochem. 198 (1991), 10). This substrate has two major disadvantages, however: while 2-naphthol has its maximum fluorescence intensity at pH 10.4, PI-PLC has an optimal pH at about pH 7.4 and is not active above pH 9.0. Therefore, a pH of 8.5 was selected for assay purposes as a compromise between retaining both sufficient fluorescence intensity of 2-naphthol as well as the pH activity profile of the enzyme. Also, specific activity was quite low in some instances.

Similar problems arose with racemic hexadecylthiophosphoryl-1-myo-inositol, a thiophosphate-containing analogue of PI (cf. E. K. Hendrickson, J. L. Johnson, H. S. Hendrickson; Bioorg. Med. Chem. Lett. 1 (1991), 615–618). The thiol released after cleavage of the substrate was determined by reaction with a colorimetric thiol reagent. The maximal activity was only about 1% of that for PI.

4-Nitrophenyl myo-inositol-1-phosphate (NPIP; cf. M. S. Shashidhar, J. J. Volwerk, O. H. Griffith, J. F. W. Keana; Chem. Phys. Lipids 60 (1991), 101; and A. J. Leigh, J. J. Volwerk, O. H. Griffith, J. F. W. Keana; Biochemistry 1992,31) was the first chromogenic substrate for which PI-PLC showed high maximal activity (150 mmol $mind^{-1}$ $mg^{-1}$ at a substrate concentration of 2 mM and pH 7.0). The substrate was used for spectrophotometric assay methods. Here, a major drawback is the low stability in aqueous buffer solutions at room temperature. Furthermore it cannot be used for plating media since the liberated 4-nitrophenolate is soluble in water and would migrate into the medium. A further disadvantage of NPIP is the yellow color of 4-nitrophenolate which may interfere with the background in culture media as well as in biological samples including body fluids.

Another prior art chemiluminescent substrate for PI-PLC, racemic 3-(4-Methoxyspiro[1,2-dioxetane-3,2'-tri-cylo-[3.3.1.1.]decan]-4-yl)-phenyl myo-inositol-1-O-hydrogen phosphate (LUMI-PI; cf. M. Ryan, J.-C. Huang, O. H. Griffith, J. F. W. Keana, J. J. Volwerk; Anal. Biochem. 214 (1993), 548), was well suited for detection of nanogram amounts of enzyme by luminometric measurement and even as little as 16 picogram of enzyme was detectable after several days using microtiter plates and autoradiography film. However, this substrate requires expensive equipment and is not suited for plating media or histochemical uses. In addition, synthesis of the substrate is not well-suited for commercial production thus making it unattractive for general practical use.

OBJECTS AND SUMMARY OF THE INVENTION

Accordingly, a main object of the present invention is to provide a novel chromogenic substrate for detecting PI-PLC, e.g. by means of conventional spectrophotometric and histochemical assays including use in plating media and which substrate is substanitally free from the disadvantages of prior art substrates enumerated above.

It has now been found, that the above and further objects will be achieved according to the invention when use is made of certain phosphodiesters, more specifically 3-indoxyl-myo-inositol-1-phosphate compounds, as said substrate. The term "3-indoxyl-myo-inositol-1-phosphate compounds" is used herein to refer to compounds of the formula (I) defined below, and to the salts thereof with organic or inorganic bases, such as ammonia (this term being used interchangeably with ammonium hydroxide, depending upon the presence or absence of water) and other bases of the type mentioned below, having no disadvantageous effect upon the stability of the formula I compounds:

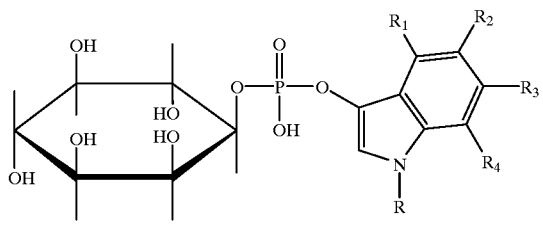

(I)

wherein R is selected from the group consisting of hydrogen and $C_{1-4}$ alkyl, such a methyl, ethyl, propyl or butyl, and $R_1$, $R_2$, $R_3$, and $R_4$ are selected from the group consisting of hydrogen and chromogenic substituents, such as halogen (e.g. F, Cl, Br, I); cyano; nitro; carboxy; amino, which may by substituted, e.g. by one or two $C_{1-4}$ alkyl groups; aminomethyl; and sulphonyl. In a preferred embodiment of formula I compounds and their salts with organic or inorganic bases. For high chromogenicity, at least one of groups $R_1$, $R_2$, $R_3$ and $R_4$ is not hydrogen so as to provide for high chromogenicity.

In a further preferred group of formula I compounds or salts thereof, R is selected from hydrogen or methyl, $R_1$ is selected from the group consisting of hydrogen and halogen (Cl preferred), $R_2$ is selected from the group consisting of hydrogen, halogen (Br preferred) and cyano, $R_3$ is selected from the group consisting of hydrogen and halogen (Cl preferred), and $R_4$ is hydrogen.

Preferred salts of formula I compounds are those formed with lithium hydroxide, sodium hydroxide, potassium hydroxide, ammonia, ammonium hydroxide, diethylamine, triethylamine, cyclohexylamine, pyridine, piperidine, piperazine, pyrrolidine, morpholine, N-methylmorpholine, p-toluidine, tetramethylammonium, and tetraethylammonium.

As will be apparent to those experienced in the art, the most preferred compounds within the scope of formula I above and the salts thereof are those which yield deeply colored (preferably blue) indigo dyes when used as substrates for detecting PI PLC, i.e. upon cleavage by PI-PLC, dimerisation, and subsequent oxidation. A few simple tests will indicate those specific compounds of formula I or their salts which are best suited for a specific substrate use. Examples of preferred formula I compounds will be given below.

Further, it will be apparent to those skilled in the art that compounds of formula I may be obtained in racemic form, and that such mixtures may be resolved to obtain the enantiomers. It is expected, however, that no substantial advantages will normally be obtained with the enantiomers. Accordingly, use of racemic mixtures of formula I compounds will be a preferred form of the invention.

The following group of compounds of formula I has been shown to be a particularly suitable group of compounds for the purposes of the present invention and, thus, constitute a preferred group: 5-bromo-4-chloro-3-indoxyl-myo-inositol-1-phosphate, 5-bromo-6-chloro-3-indoxyl-myo-inositol-1-phosphate, 6-chloro-3-indoxyl-myo-inositol-1-phosphate, and 6-fluoro-3-indoxyl-myo-inositol-1-phosphate. The salts of the above compounds with an organic or inorganic base, such as typically the ammonium salts, represent a preferred group of formula I compounds according to the invention.

According to a preferred embodiment of the present invention, compounds of formula I and the salts thereof as defined above are used as a chromogenic substrate for the detection of phosphatidylinositol-specific phospholipase C (1-phosphatidyl-D-myo-inositol inositolphospho-hydrolase or "PI-PLC").

Thus, the method of detecting PI-PLC according to the invention comprises the use of a chromogenic substrate containing at least one compound of formula I or a salt thereof.

While no theoretical limitation is intended, the efficacity of compounds of formula I and the salt thereof as substrates for PI-PLC detection is believed to reside in the fact that cleavage of a substrate according to the invention by bacterial PI-PLC results mainly in the formation of inositol 1,2-cyclic phosphate and 5-bromo-4-chloro-3-indoxyl which—after dimerisation—can subsequently be oxidized by atmospheric oxygen or another oxidant to a deep blue indigo dye suitable for sensitive chromoscopic detection by conventional methods and apparatus.

Since it is known that PI-PLCs are secreted by several human pathogens, notably Listeria monocytogenes, the invention provides, inter alia, a method of detecting such pathogens by means of the novel substrate, e.g. by screening for bacterial enzyme production directly on plating media, for example, of clinical samples or cultures isolated from food.

PREFERRED EMBODIMENTS OF THE INVENTION

A preferred specific compound for use according to the invention is the ammonium salt of the compound of formula IV below, i.e. 5-bromo-4-chloro-3-indoxyl myo-inositol-1-phosphate; the ammonium salt of the formula IV compound will be referred to as "X-phos-inositol" herein below:

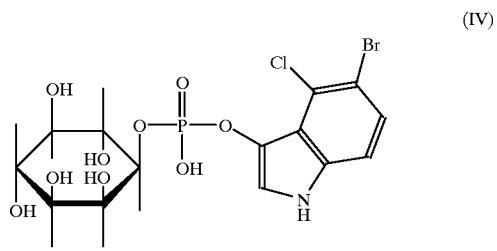

(IV)

Compounds of formula I or their salts can be obtained generally by treating, in a first process step, the corresponding indoxyl-3-dichloro phosphates of formula II given below with a reactive inositol compound, e.g. a OH-protected inositol having a free hydroxyl group in 1-position (termed "G-Ins-OH" below) so as to obtain an intermediate compound III, e.g. by stirring the reactants in an organic base, such as pyridine, N-methyl morpholine, or triethylamine, as a reaction medium at ambient temperature during a period of several hours (e.g. 1–10 hours). Preferably, intermediate compound III is converted into a salt with an organic or inorganic base, such as ammonium hydroxide, before proceeding to the second reaction step:

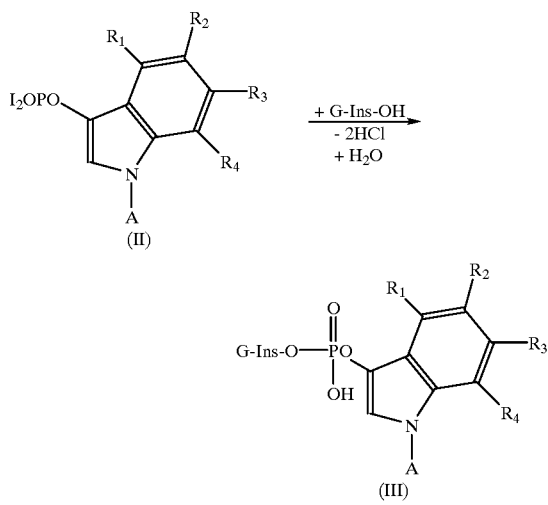

in which A is hydrogen or a conventional N-protecting group, such as $C_{1-4}$ alkyl (preferably methyl); acyl (preferably acetyl; or N-protecting groups commonly known as Boc, Fmoc, etc., and G is an OH protecting group on each hydroxyl of inositol except the 1-hydroxy; typical examples for G include optionally substituted benzyl, optionally substituted $C_{3-6}$ alkylidene (e.g. isopropylidene, cyclopentylidene or cyclohexylidene); and optionally substituted tetrahydropyranyl.

In the subsequent second reaction step, all protecting groups G and optional N-protecting group on the formula III intermediate are removed, e.g. by hydrogenolysis or acidic cleavage, depending upon the nature of the OH-protecting groups; if A is an N-protecting group it can be removed by conventional methods of peptide chemistry, e.g. alkaline hydrolysis.

It will be apparent from the above that compounds of formula I for use as substrates including the preferred X-phosinositol can be manufactured efficiently in sufficiently large quantities as are required for application in standard screening procedures.

The preferred novel substrate compound of formula IV, i.e. 5-bromo-4-chloro-3-indoxyl myo-inositol-1-phosphate in the form of the ammonium salt of the formula IV, or X-phosinositol, is a colorless watersoluble substance having an UV-maximum (in Tris/HCl-buffer at pH 7) at 290 nm with an absorption coefficient of 5000 l mol$^{-1}$ cm$^{-1}$. The 5,5'-dibromo-4,4'-dichloro-indigo generated by the PI-PLC detection method according to the invention (i.e. upon cleavage of the substrate by PI-PLC, dimerization and subsequent oxidation) is a dye known per se and has a broad absorption maximum ranging from approximately 500 nm to 700 nm with two peaks near 615 and 650 nm. The indigo dye is intensely coloured with an absorption coefficient near 6000 l mol$^{-1}$ cm$^{-1}$. The dye stays dissolved in buffer solutions for at least about 24 hours but tends to precipitate partially upon standing for longer periods.

Based upon tests made with X-phos-inositol it is expected that the novel substrates according to the invention are stable if stored during extended periods at temperatures below about -15° C. and protected from light. Also, X-phosinositol proved to be stable in conventional buffer solutions (Hepes/NaOH; Tris/HCl)for several days at pH 7 and room temperature. Thus, problems with background signals as was the case with some prior art substrates caused by slow hydrolysis of the substrate in the buffer media, are avoided and, again, similar properties can be expected for other formula I compounds.

According to an important embodiment of the invention the novel substrate of formula I, preferably the salts of the compound of formula IV with an organic or inorganic base, such as ammonia or ammonium hydroxide, is used for a sensitive spectrophotometric assay of PI-PLC from *Bacillus cereus*; in this embodiment, the substrate is used in combination with serum albumin, e.g. bovine serum albumin (BSA) or, alternatively, with a surfactant.

In the absence of such additives only a weak signal is detected after a few hours with no further increase. It must be emphasized in this context that it is known per se that surfactants may enhance the activity of PI-PLC, possibly by promoting formation of molecular aggregates or micelles thus creating a lipophilic environment for the enzyme. Accordingly, selection of a suitable detergent is within the competence of those skilled in the art and does not need a more detailed general discussion. It is a reasonable assumption that the hydrophobic nature of BSA enhances enzymatic reactions.

Substrates using 5-bromo-4-chloro-3-indoxyl as chromophor are suitable for the detection of various enzymes on culture media, e.g. X-Gal for β-galactosidase or X-glucuronic acid sodium salt for β-glucuronidase. In such assay procedures, the deep blue 5,5'-dibromo-4,4'-dichloro-indigo dye (resulting from cleavage of the substrate by the specific enzyme, dimerization and subsequent oxidation) gives a characteristic, strongly coloured precipitate on plating media which is clearly distinguished from even a yellow background as is encountered frequently. Furthermore the insolubility prevents migration of the dye throughout the plate.

Thus it can safely be expected that the novel media of formula including the preferred X-phos-inositol will generally improve and facilitate detection of PI-PLC producing colonies of bacteria.

BRIEF DESCRIPTION OF THE DRAWINGS

The invention will now be explained in more detail by way of examples and with reference to the encolsed drawings in which.

Figure 1:
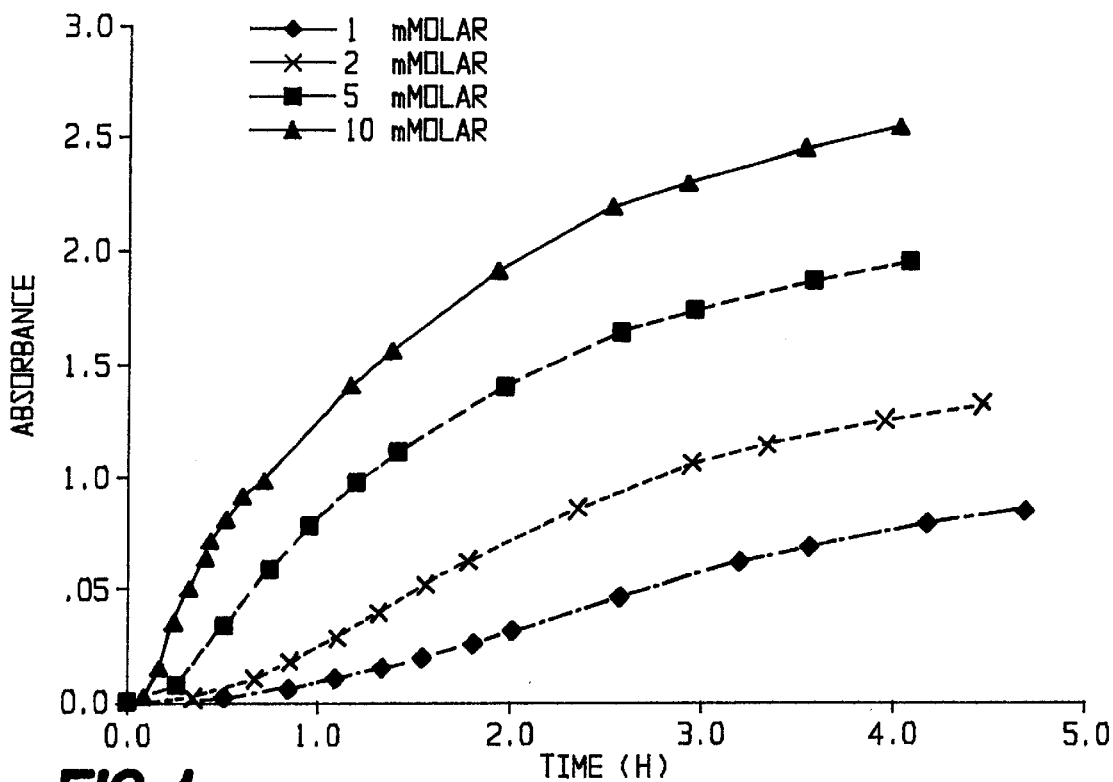
FIG. 1 is a graph showing dependence of the absorbance (on the ordinate) upon time (on the abscissa) at various substrate concentrations.

It is to be noted, however that the specific examples are not intended to limit the invention in any way.

EXAMPLES

Preparation of the New Substrates

Example 1

Preparation of X-phos-Inositol

1-Acetyl-5-bromo-4-chloro-3-indoxyl-dichlorophosphate (cf. J. P. Horwitz et al; J. Med.Chem. 13 (1970) 1024) and 2,3:5,6-Di-isopropylidene-4-(4-methoxy-tetra-hydropyran- 4-yl-)-myo-inositol (cf. M. S. Shashidar et al, Chem. Phys. Lipids 60 (1991) 101) were prepared as described in the literature just cited.

Step 1: Preparation of the ammonium salt of 1-acetyl-5-bromo-4-chloro-3-indoxyl [2,3:5,6-di-isopropylidene-4-(4-methoxytetra-hydropyran-4-yl)-myo-inositol]-1-phosphate 1-Acetyl-5-bromo-4-chloro-3-indoxyl-dichlorophosphate (2.18 g, 5.38 mmol) was suspended under nitrogen in dry pyridine (20 ml) and 2,3:5,6-Di-isopropylidene-4-(4-methoxy-tetrahydropyran-4-yl-)-myo-inositol (1.12 g, 3.0 mmol) was added after 10 minutes. The mixture was well stirred overnight.

The brown solution containing some solid matter was cooled in an ice bath; then, water (5 ml) was added so that the temperaturere rose to 18° C. and the solid dissolved rapidly.

After removing the ice bath, chloroform (30 ml) was added. The solution was then stirred for an additional period of 10 min. The organic phase was separated and the aqueous phase was extracted with chloroform(10 ml).

The combined organic phases were extracted once with water and finally dried over anhydrous sodium sulfate. The clear yellow solution obtained was passed through a column of silica gel (60–230 μm, Merck # 7734, 17 g) and the eluate discarded. The column was eluted with chloroform (50 ml)for removing the pyridine. The product was then isolated as its ammonium salt by elution with chloroform/methanol/25% aqueous ammonia solution 70:30:1 (180 ml) and concentration of the eluate in vacuo.

The yellow-brown, clear oil was taken up in chloroform (10 ml) and re-evaporated in vacuo leaving a brownish amorphous solid (1.91 g, 85% yield); m.p. 89–91° C.

Step 2: Preparation of the ammonium salt of 1-acetyl-5-bromo4-chloro-3-indoxyl myo-inositol-1-phosphate 1-Acetyl-5-bromo-4-chloro-3-indoxyl [2,3:5,6-di-isopropylidene-4-(4-methoxy-tetra-hydropyran-4-yl)-myo-inosi-tol]-1-phosphate in the form of the ammonium salt (1.12 g, 1.5 mmol) was suspended in acetic acid/water 1:4 (50 ml) and stirred overnight at ambient temperature. The turbid solution obtained was extracted three times with ether (20 ml) and the pale yellow aqueous solution filtered and co-evaporated with ethanol (10 ml).

Ethanol (10 ml) was added to the clear greenish-yellow oil; the resulting solution was evaporated again once to obtain the crude product as a light-yellow resin (0.80 g, 97% yield).

An analytically pure sample was obtained by crystallization from water/ethanol: m.p. 123–125° C. 200 MHZ-NMR (D$_2$O) d 2.50 (s, 3H), 3.30 (t, 1H), 3.45–3.65 (m, 2H), 3.75 (t, 1H), 4.10 (t, 1H), 4.30 (broad s, 1H), 7.25 (d, 1H), 7.45 (s, 1H), 7.70 (d, 1H).

Step 3: Preparation of the ammonium salt of 5-bromo-4-chloro-3-indoxyl myo-inositol-1-phosphate X-phos-inositol)

The crude ammonium salt of 1-acetyl-5-bromo-4-chloro-3-indoxyl myo-inositol-1-phosphate(0.55 g,1 mMol) obtained in the preceding step was added to a 2 N solution of gaseous ammonia in methanol (5 ml, Aldrich # 34,142-8) and stirred under nitrogen for three hours at ambient temperature. The oil slowly dissolved while the solution gradually turned green.

The solution was evaporated in vacuo (40° C.), methanol (5 ml) was added and the green solution evaporated again once. The amorphous green colored solid was dissolved in water (10 ml), treated with activated carbon and then extracted with ethyl acetate (3×5 ml).

The aqueous phase was again evaporated to obtain a yellow oil. The crude oil was well stirred while methanol (10 ml) was slowly added. A fine solid precipitated from the solution. Ethanol (20 ml) was added dropwise to the suspension while stirring. The product was collected thereafter by filtration through a glass filter funnel. Thus 0.22 g (44% yield) of a slightly off-white powder was obtained.

Analyses calcd. for $C_{14}H_{19}BrClN_2O_9P$ (MW=505.64): C 33.26, H 3.79, N 5.54, Cl 7.01; Found (dried substance): C 33.44, H 3.92, N 5.42, Cl 7.13. 200 MHz-NMR (D$_2$O) d 3.40 (t, 1H), 3.55–3.75 (m, 2H), 3.85 (t, 1H), 4.20 (t, 1H), 4.30 (broad s, 1H), 7.10 (d, 1H),7.25 (d, 1H), 7.30 (s, 1H).

Examples 2–4

Spectrophotometric Assays of PI-PLC using X-phos-inositol

In the following examples 2–4, a Perkin-Elmer Lambda 15 Spectrophotometer was used for the experiments. The experiments were conducted at ambient temperature (about 25° C.).

The procedure for the detection of PI-PLC was as follows: X-phos-inositol was dissolved in 0.1 M Hepes/NaOH-buffer or Tris/HCl-buffer of pH 7.0 containing 0.1% of bovine serum albumin (BSA).

Instead of BSA, a surfactant, such as deoxycholic acid sodium salt, Triton X-100 or octylglucoside was used. In these cases, the rates of cleavage were somewhat smaller (cf. FIG. 5).

3.5 ml of the solution were transferred to a cuvette and the spectrometer was set to 650 nm. After adding an aliquot from a stock solution of PI-PLC (Boehringer Mannheim # 1143 069; specific activity 600 U/mg, 5U/100 μl solution, corresponding to 8.33 μg/100 μl) the photometer readings were noted after defined periods of time for different substrates and enzyme concentrations, respectively.

Alternatively, the absorbance was measured directly by the spectrometer during several hours.

Example 2

Dependence Upon Substrate Concentration

FIG. 1 shows the time dependence of the absorbance at 650 nm for various substrate concentrations.

In each case, the amount of enzyme added was 0.167 μg (2 ml stock solution), and 0.1% BSA were used as additive. The appearance of the indigo color was retarded.

The sigmoidal form of the lines indicate a rather complex kinetic. This might from the need to form a complex of the BSA, the enzyme and the substrate. The delay might also be attributed to dimerization and oxidation subsequent to enzymatic cleavage of the substrate.

Accordingly, the initial rates of cleavage of X-phos-inositol by PI-PLC were not linear with time, but there was a linear area in each case which was used to determine the specific enzyme activities for each concentration (cf. Table 1).

The specific activity at a substrate concentration of 5 mMol approximates 60 μMol min$^{-1}$ (mg$^{-1}$ protein) and similar results were found for NPIP.

TABLE 1

Dependence of rate of cleavage and specific activity on substrate concentration

| Substrate concentr. [mMol] | Rate [nMol/min] | Specific Activity [μMol min$^{-1}$ mg$^{-1}$] |
|---|---|---|
| 1 | 2.8 | 17 |
| 2 | 4.8 | 29 |
| 5 | 10.2 | 61 |
| 10 | 14.0 | 84 |

Example 3
Dependence on Enzyme Concentration

Figure 2:
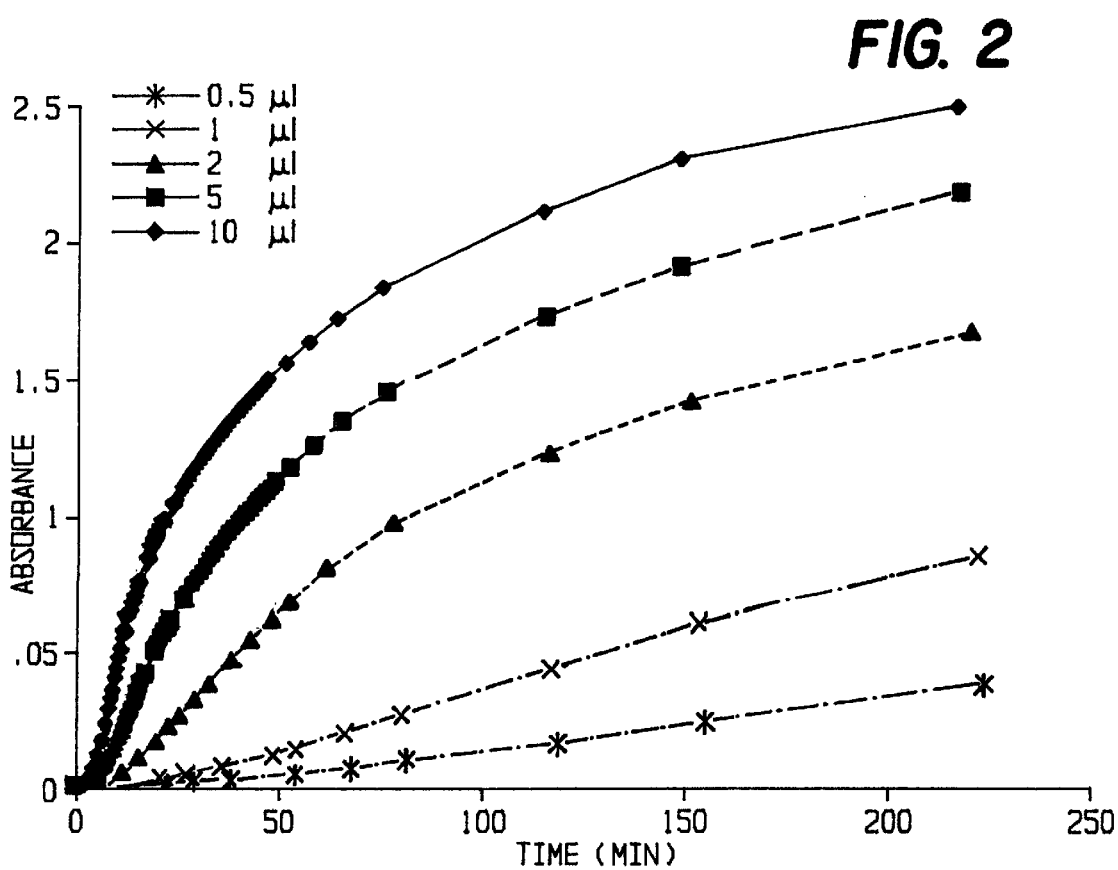
FIG. 2 is a graph similar to that of FIG. 1 except that the curves are shown for various enzyme concentrations.
Figure 3:
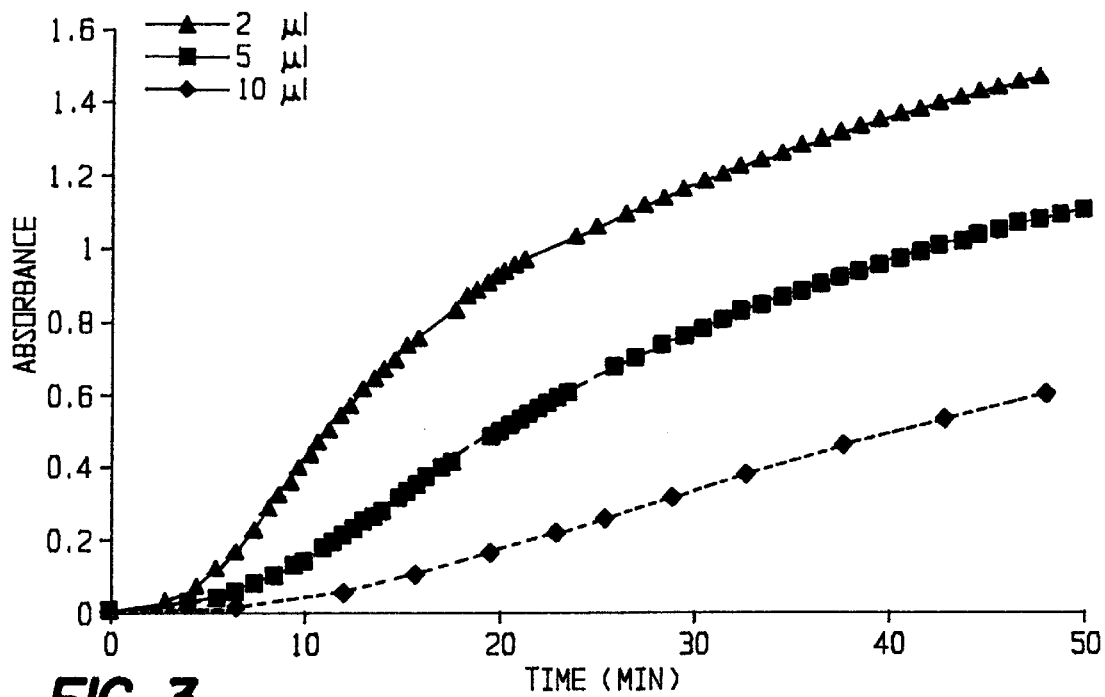
FIG. 3 is a graph similar to that of FIG. 2 for another group of tests.

FIGS. 2 and 3 show the change of absorbance as a function of time for different enzyme concentrations at a substrate concentration of 5 mM and addition of BSA.

The linear areas could be used to determine enzyme concentrations. The rates of cleavage [nMol/min] and the specific enzyme activities are as shown in Table 2.

Figure 4:
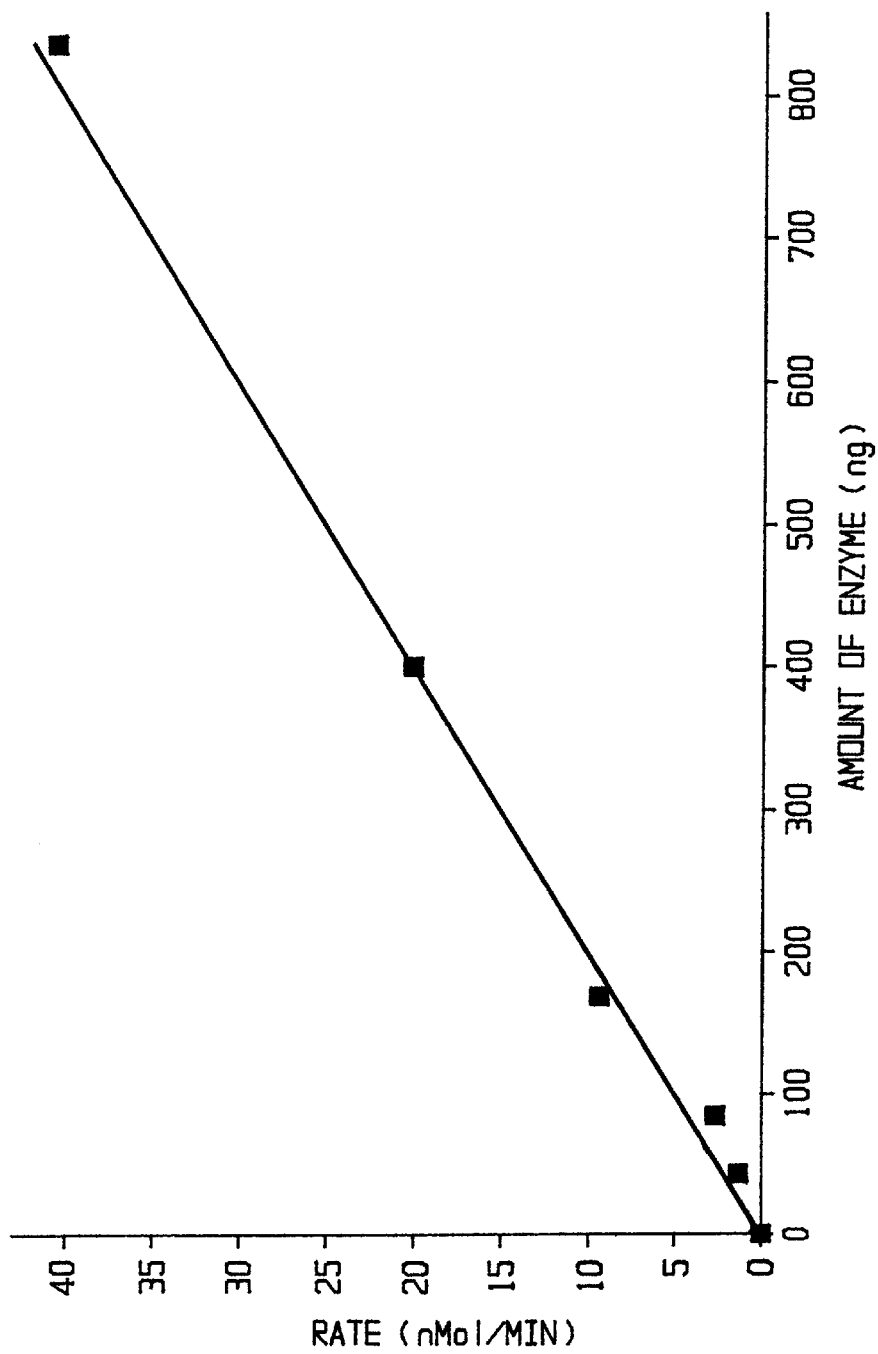
FIG. 4 is a graph showing the rate of substrate cleavage (ordinate, in nMol/min) as a function of the amount of enzyme (abscissa, in nanogramms, and FIG. 5 is a graph similar to FIG. 1 showing the resuits of adding BSA and of various surfactants.

A plot of the cleavage rates versus amount of enzyme added (cf. FIG. 4) indicated satisfactory linearity for the higher range of values (addition of 2, 5 and 10 μl stock solution, and 167, 416 and 833 ng of enzyme, respectively) and a decrease for the lower range of values (0.5 and 1 μl, or 42 and 83 ng enzyme, respectively).

TABLE 2

Dependence of rate of cleavage and specific activity on enzyme concentration

| Amount of enzyme | | Rate | Spec. Activity |
|---|---|---|---|
| [μl stock sol.] | [ng] | [nMol/min] | [μMol min$^{-1}$ mg$^{-1}$] |
| 0.5 | 42 | 1.3 | 31 |
| 1 | 83 | 2.8 | 33 |
| 2 | 167 | 9.4 | 56 |
| 5 | 416 | 21.0 | 50 |
| 10 | 833 | 41.0 | 49 |

The limit of detection or sensitivity at a substrate concentration of 5 mM is far below 10 ng of enzyme.

Example 4
Use of BSA and Surfactants as Enhancers

Figure 5:
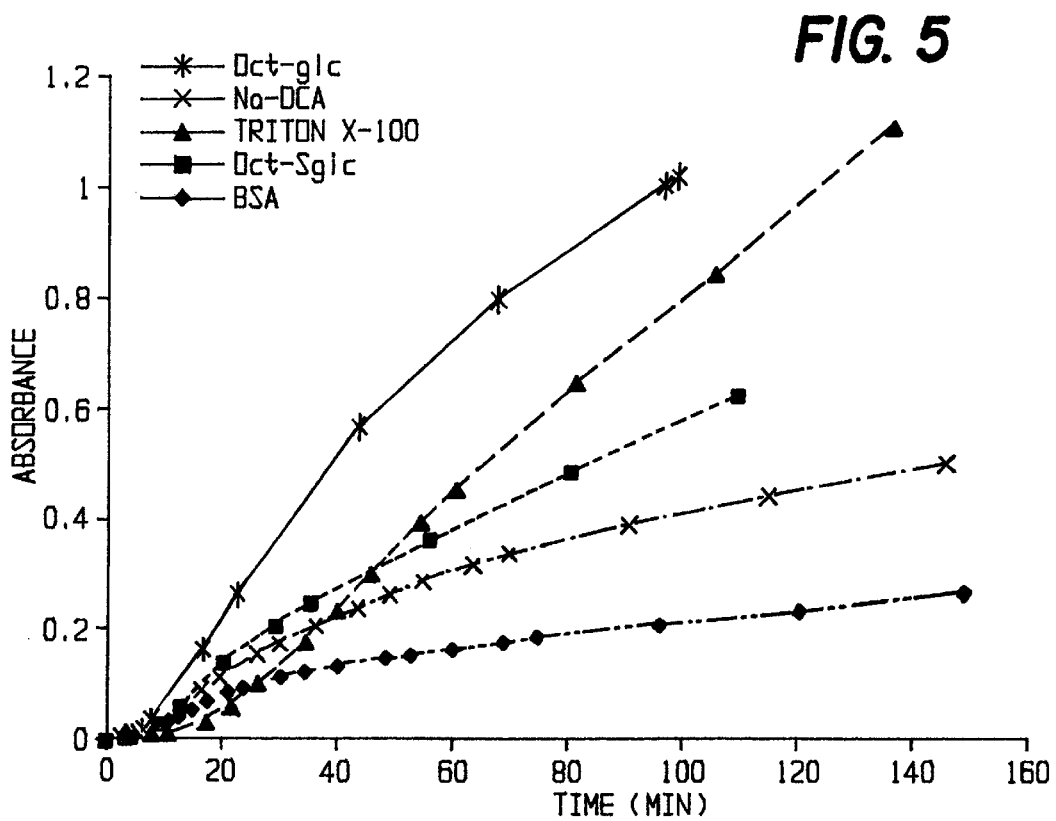

FIG. 5 shows a comparison of the enzymatic cleavage of X-phos-inositol using different enhancer additives.

The conditions of each test run were as follows: substrate concentration 5 mMol; 416 μg enzyme (5 μl stock solution); enhancer 0.1%.

All surfactants tested increased the reaction rate significantly yet in a different manner: deoxycholic acid in the form of the sodium salt (Na-DCA) and Triton X-100 had the strongest effect while the absorbance early flattened and reached only a relatively low plateau when using octylthioglucoside (Oct-Sglc) and, notably, octylglucoside (Oct-glc). Furthermore, with Na-DCA, Oct-glc and Oct-Sglc the dye precipitates after standing overnight. Accordingly, BSA was best suited as an enhancer additive in view of sensitive of a PI-PLC assay.

It should be noted that while the above examples are concerned with X-phos-inositol, the preferred substrate of formula IV, it is apparent from the general disclosure above that similar results will be obtained with other substrates of formula if the substituents $R_1, R_2, R_3, R_4$ of the benzene nucleus of the formula I compounds are selected in a manner known, per se, in the chemistry of indigo-type dyes. Generally, the invention provides for safe, sensitive and commercially viable detection of potentially pathogenic bacterial activity of such microbes as *Bacillus cereus, B. Thuringiensis, Staphylococcus aureus* and various Listeria strains in potentially infected materials including physiological samples or consumable goods such as foods and beverages. Thus, various modifications of the examples given above will be apparent. The scope of the invention is to be construed on the basis of the following claim.

Although certain presently preferred embodiments of the present invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

What is claimed is:

1. A method of detecting a phosphatidylinositol-specific phospholipase C enzyme comprising the steps of:

contacting a sample suspected of containing said phosphatidylinositol-specific phospholipase C enzyme with a substrate comprising a chromophoric portion, said substrate being susceptible to cleavage by said enzyme and yielding a dye when said chromophoric portion of the substrate is dimerized and oxidized; said substrate is a 3-indoxyl-myo-inositol-1-phosphate compound of formula (I)

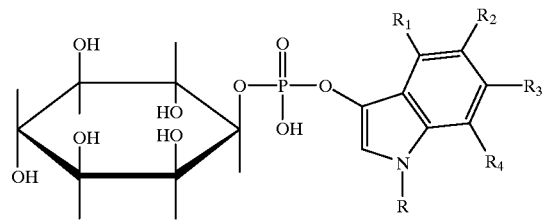

(I)

wherein R is selected from the group consisting of hydrogen and $C_{1-4}$ alkyl, while $R_1$, $R_2$, $R_3$, and $R_4$ are radicals independently selected from the group consisting of hydrogen halogen, cyano, nitro, carboxy, amino, amino substituted with $C_{1-4}$ alkylgroups, aminomethyl, and sulphonyl; or a salt of compound (I); and monitoring for color formation as a consequence of said sample suspected of said phosphatidylinositol-specific phospholipase C enzyme.

2. The method of claim 1, wherein R is selected from the group consisting of hydrogen and methyl; $R_1$ is selected from the group consisting of hydrogen and halogen; $R_2$ is selected from the group consisting of hydrogen, halogen and cyano; $R_3$ is selected from the group consisting of hydrogen and halogen; and $R_4$ is hydrogen.

3. The method of claim 1, wherein said salt is a salt formed of said compound (I) with a member selected from the group consisting of lithium hydroxide, sodium hydroxide, potassium hydroxide, ammonia, diethylamine, triethylamine, cyclohexylamine, pyridine, piperidine, piperazine, pyrrolidine, morpholine, N-methylmorpholine, p-toluidine, tetramethylammonium, and tetraethylammonium.

4. The method of claim 2, wherein said substrate is the ammonium salt of 5-bromo-4-chloro-3-indoxyl myo-inositol-1-phosphate represented by formula (IV)

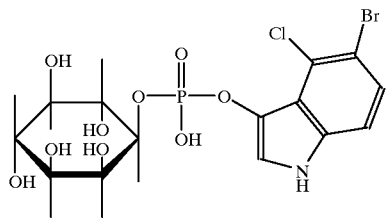

(IV)

or a salt thereof.

5. The method of claim 1, wherein said substrate of compound I or said salt thereof is used in combination with at least one additive selected from the group consisting of serum albumin and surfactants.

6. The method of claim 5, wherein said salt is a salt formed of said compound I and a member selected from the group consisting of lithium hydroxide, sodium hydroxide, potassium hydroxide, ammonia, diethylamine, triethylamine, cyclohexylamine, pyridine, piperidine, piperazine, pyrrolidine, morpholine, N-methylmorpholine, p-toluidine, tetramethylammonium, and tetraethylammonium.

7. The method of claim 1, wherein said phosphatidylinositol-specific phospholipase C enzyme is taken from a pathogen selected from the group consisting of *Bacillus cereus, Bacillus thuringiensis, Listeria monocytogenes, Listeria ivanovii* and *Staphylococcus aureus*.

* * * * *